(12) United States Patent
Chatterjee

(10) Patent No.: US 6,511,979 B1
(45) Date of Patent: Jan. 28, 2003

(54) METHODS FOR TREATING CONDITIONS MODULATED BY LACTOSYLCERAMIDE

(75) Inventor: Subroto Chatterjee, Columbia, MD (US)

(73) Assignee: Johns Hopkins University, Baltimore, MD (US)

(*) Notice: Subject to any disclaimer, the term of this patent is extended or adjusted under 35 U.S.C. 154(b) by 0 days.

(21) Appl. No.: 09/359,023

(22) Filed: Jul. 22, 1999

Related U.S. Application Data

(60) Provisional application No. 60/094,298, filed on Jul. 27, 1998.

(51) Int. Cl.[7] .................... A61K 31/535; A61K 31/445; A61K 31/40
(52) U.S. Cl. .................... 514/237.8; 514/315; 514/428
(58) Field of Search .............................. 514/237.8, 315, 514/428

(56) References Cited

U.S. PATENT DOCUMENTS

| | | | |
|---|---|---|---|
| 5,041,441 A | 8/1991 | Radin et al. | 514/237.8 |
| 5,302,609 A | 4/1994 | Shayman et al. | 514/380 |
| 5,339,567 A | 8/1994 | Platt et al. | 514/56 |
| 5,656,641 A | 8/1997 | Platt et al. | 514/315 |
| 5,707,649 A | 1/1998 | Inokuchi et al. | 424/450 |
| 5,801,185 A | 9/1998 | Platt et al. | 514/315 |
| 5,972,928 A | 10/1999 | Chatterjee | 514/212 |

OTHER PUBLICATIONS

Masaru Kubota, et al., "Sphingolipid biosynthesis by L–PDMP after rat MCA occl", Abstract, 2 pages Acta Neurochir. Suppl.. 76:339–41 (2000).

S. Chatterjee, et al. "Studies Of The Action Of Ceramide–like Substances (D– and L–PDMP) On Sphingolipid Glycosyltransferases And Purified Lactosylceramide Synthase", Glycoconjugate Journal (1996) 13: 481–486.

A. Bhunia et al., *J. Bio. Chem.*, 272:15642–45649 (1997).

S. Chatterjee et al. *Glycobiology*, pp. 303–311 (1996).

N. Radin et al., *Adv. in Lipid Res.*, 26:183–213 (1993).

C. Rani et al., *J. Bio. Chem.*, 270:2859–2867 (1995).

A. Abe et al., *Biochimica et Biophysica Acta*, 1299:333–341 (1996).

G. Shukla et al., *Biochimica et Biophysica Acta.*, 1083:101–108 (1991).

J. Inokuchi et al., *J. Lipid Res.*, 28:565–571 (1987).

A. Shukla et al., *J. Lipid Res.*, 32:713–722 (1991).

J. Tardif et al., *New Eng. J. Med.*, 337:365–372 (1997).

A. Abe et al., *J. Lipid Res.*, 36:611–621 (1995).

S. Chatterjee, *Mol. Cell Biochem.*, 111(1–2):143–147 (1992).

S. Chatterjee et al., *Glycobiology*, 7:57–65 (1997).

S. Chatterjee et al., *J. Lipid Res.*, 37:1334–1344 (1996).

N. Radin, *Mol.& Chem. Neuropathology*, 21:111–127 (1994).

T. Hanichen et al., *Laboratory Animal Sci.*, 47:275–279 (1997).

S. Chatterjee, *Biochemical& Biophysical Res. Comm.*, 181:554–561 (1991).

The Merck Index, Eleventh Edition (1989).

*Primary Examiner*—Revecca Cook
(74) *Attorney, Agent, or Firm*—Peter F. Corless; Robert L. Buchanan; Dianne M. Rees

(57) ABSTRACT

The present invention includes methods for treatment and prophylaxis of conditions associated with lactosylceramide. The methods generally provide for administration to a mammal, particularly a human, of a therapeutically effective amount of a compound that increases enzymatic activity of UDPGal:GlcCerβ1→4 galactosylceramide (GalT-2). In vitro and in vivo assays for detecting compounds with therapeutic capacity to modulate GalT-2 are also provided.

36 Claims, 4 Drawing Sheets

METHODS FOR TREATING CONDITIONS MODULATED BY LACTOSYLCERAMIDE

This application claims the benefit of U.S. Provisional Application No. 60/094,298 filed on Jun. 27, 1998.

BACKGROUND OF THE INVENTION

1. Field of the Invention

The present invention includes methods for treating conditions modulated by lactosylceramide and, more particularly, to the use of one or more compounds that enhance UDP-galactose, GlcCer, β1→4 galactosyltransferase (GalT-2) activity to treat a subject suffering from or susceptible to a condition caused or contributed to by lactosylceramide. The present invention also relates to methods for detecting and analyzing compounds with therapeutic capacity to treat such conditions.

2. Background

Inappropriate cell proliferation in an organism can modulate the development or severity of a variety of conditions. For example, there is recognition that certain conditions can be treated or prevented by increasing cell proliferation in adult or pre-adult animals. In particular, it has been proposed that conditions relating to infection, ulceration, degeneration (e.g., apoptotic and necrotic cell death), aging, hematopoiesis, angiogenesis, certain immune responses, cell and tissue repair can be positively impacted by increasing the proliferation of specified cells. See generally Alberts, B. et al. (1989) in *Molecular Biology of the Cell 2$^{nd}$* ed. Garland Publishing Co. (New York and London); Kandel, E. R et al. (1991) in *Principles of Neuroscience*, Apppleton & Lange, (Norwalk, Conn.); Cold Spring Harbor Conf. *Cell Proliferation* (1979), Cold Spring Harbor Laboratories, (New York); *Tissue Growth Factors*, (1981) R. Baseega, ed., (Springer-Verlag, New York).

The proliferation of particular animal cells has attracted interest. For example, the proliferation of smooth-muscle cells (SMCs), epithelia, and other intima has been reported to effect vascular development and integrity, e.g., as in vascular malformation and formation of vascular lesions. In addition, the proliferation of certain skin cells is believed to enhance responses to various traumata such as wounding (e.g., following thermal injury). It is particularly recognized that SMCs and epithelia have significant roles in angiogenesis. See e.g., *Tissue Growth Factors*, supra; Folkman and Shing (1992), *J. Biol. Chem.* 267: 10931.

The proliferation of cells associated with heart, brain, liver, kidney, eye and other organs has also attracted attention. For example, it has been suggested that increasing numbers of specified cells can treat or prevent certain neurodegenerative diseases such as those impacting the central and peripheral (e.g., motor) systems. Degenerative diseases of the retina and other eye structures can lead to progressive deterioration of vision. In particular, age-related macular dystrophies (e.g., Stargardt disease) are believed to be negatively impacted by inappropriate proliferation of certain cells, e.g., macula. It is has been proposed that the effect of many, if not all neurodegenerative disorders can be offset by enhancing the proliferation of specified cells. See e.g., Kusiak, J. W et al (1996) *Mol. Chem. Neuropathol.* 153; Kandel, E. R et al. supra; Neary et al. (1996) *Trends Neurosci.* (1996) 13.

There has been recognition that inappropriate cell adhesion can also contribute to some conditions. For example, it has been suggested that blood coagulation is enhanced by adhesion of platelets and perhaps other blood cells to injured vessels. In addition, certain immune responses, e.g., inflammation associated with rejection of foreign bodies, and recruitment of immune cells are believed to be enhanced in many cases by cell adhesion. Increased adhesion of certain cells may also augment angiogenesis following trauma, during development or following grafting.

A variety of synthetic, semi-synthetic and naturally-occurring cell molecules have been reported to play significant roles in animal cell proliferation. Such molecules include certain cytokines, growth factors, cell receptors, matrix molecules, enzymes, second messenger molecules (e.g., cyclic nucleotides) transcription factors, and mitogens such as phorbol esters.

Other molecules such as adhesion molecules appear to have significant roles in initiating and maintaining suitable cell-to-cell contact.

More particularly, molecules with capacity to modulate cell pathways comprising glycosphingolipids (GSLs).have attracted substantial interest. The GSLs have been reported to have roles in the proliferation and adhesion of animal cells among other functions. See e.g., Chatterjee, S., *Biochem. Biophys. Res Comm.* (1991) 181:554; Hakomori, S. I. (1983) in *Sphingolipid Chemistry*, eds. Kanfer, J. N. and Hakomori, S. I. (Plenum Press, New York); Obeid, L. M et al. (1993) *Science* 259: 1769 and references cited therein.

Specific cell pathways relating to GSLs such as glucosylceramide (GlcCer) and lactosylceramide (LacCer) have been disclosed. For example, one pathway involves synthesis of GlcCer by coupling UDP-glucose to ceramide in a reaction catalyzed by UDP-glucose glucosyltransferase (GlcT-1). Another step converts the GlcCer to LacCer using UDP-galactose, GlcCer, β1→4 galactosyltransferase (GalT-2). See e.g., Chatterjee et al. supra.

Attempts have been made to inhibit the steps involving GlcT-1. For example, it has been reported that the D-enantiomer of 1-phenyl-2-decanolylamino-3-morpholino-1-propanol (D-PDMP) inhibits GlcT-1 and reduces proliferation of vascular cells. The mechanism of PDMP action has been reported to be unclear. See e.g., Felding-Habermann, B., et al. (1991) *Biochemistry* 29:6314; Shukla, G. S. et al. *Biochem. Biophys. Acta.* (1991) 1083:101; Inokuchi, J. et al., *J. Lipid. Res.* (1987) 28:565; and Chatterjee, S., supra.

Specified morpholinoceramides also have been disclosed as GlcT-1 inhibitors. See Carson, K. and B. Ganem (1994) *Tetrahedron Lets.* 35:2659.

Increased levels of LacCer are believed to enhance the proliferation of certain animal cells such as aortic smooth-muscle cells and specified melanoma cells. See e.g., Chatterjee, S., supra and Noirijiri, H. Et al (1988) *J. Biol. Chem.* 263:443.

Thus, it would be desirable to have effective methods of modulating levels of LacCer e.g., by enhancing GalT-2 activity. In particular, it would be useful to have therapeutic methods of increasing LacCer levels to treat or prevent conditions or diseases impacted by lactosylceramides.

SUMMARY OF THE INVENTION

We have now discovered therapies to treat or prevent various conditions or diseases modulated by lactosylceramide (LacCer). In particular, we have discovered therapies that include increasing activity of UDP-galactose, GlcCer, β1→4 galactosyl-transferase (GalT-2).

More specifically, the invention provides methods for treatment or prevention of conditions or diseases impacted by increased cell proliferation or adhesion, e.g., tissue repair, ulceration, blood coagulation, infection, degeneration (e.g., apoptotic and necrotic cell death), angiogenesis, aging and certain immune responses and chemoattraction.

Therapies of the invention are particularly effective for enhancing tissue repair and for the treatment or prevention of undesired degeneration particularly involving cells such as neurons of the central (CNS) or peripheral (PNS) nervous system including the eye. In one protocol of the invention, an increase in cell proliferation following cell or tissue contact with one or more compositions of the invention can be observed, whereas a control exhibits much less proliferation. In particular, the present invention features a variety of in vitro and in vivo protocols for testing the compositions as set forth in the discussion and examples which follow.

LacCer-modulated conditions that can be enhanced in accordance with the invention also include angiogenesis (neovascularization); and response to various traumata e.g., ulceration of smooth muscle and related cells; tissue repair, particularly in response to burning or an incision; and grafting.

Therapeutic methods of the invention in general comprise administering to a subject, particularly a mammal such as a primate and especially a human, in need of treatment a therapeutically effective amount of a compound that can promote GalT-2 activity. Preferably, an administered compound increases cell proliferation by at least about 15% or 25% in a standard in vitro cell proliferation assay. Examples of such an assay are described below. It is generally preferred that the administered compound exhibits an $EC_{50}$ of at least about 10 $\mu M$ in a standard in vitro GalT-2 assay as defined below, more preferably an $EC_{50}$ of about 1 $\mu M$ or less, still more preferably an $EC_{50}$ of about 0.001 $\mu M$ or less in a standard in vitro GalT-2 assay as defined below. As defined herein, the $EC_{50}$ is a concentration of the cell proliferation enhancing compound that exhibits at least about 10% to 20% stimulation of cell proliferation with respect to a suitable control as described below. Such compounds that can enhance GalT-2 activity are generally referred to herein as "GalT-2 enhancing compounds" or other similar term.

Compounds suitable for use in the treatment methods of the invention are generally levorotatory and include those of the following Formula I:

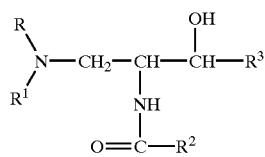

wherein R, $R^1$, $R^2$ and $R^3$ are as defined below; and pharmaceutically acceptable salts of such compounds.

The term "levortatory" (as opposed to "dextrorotatory") is used herein to denote compounds of Formula I that have capacity to rotate polarized light counterclockwise, ie. in the L or (−) direction as specifically defined below. Preferred Formula I compounds exhibit a specific optical rotation of at least −5, 10, −20, −30, −50, −100, −200 up to about −300 degrees relative to a suitable optically inactive compound.

Specifically preferred enhancing compounds for use in the therapeutic methods of the invention include L-enantiomers of the following compounds:

1-phenyl-2-decanoylamino-3-morpholino-1-propanol;
1-phenyl-2-hexadecanoylamino-3-morpholino-1-propanol;
1-phenyl-2-hexadecanoylamino-3-piperidino-1-propanol;
1-phenyl-2-hexadecanoylamino-3-pyrrolidino-1-propanol;
1-morpholino-2-hexadecanoylamino-3-hydroxyoctadec-4,5-ene; and
1-pyrrolidino-2-hexadecanoylamino-3-hydroxyoctadec-4,5-ene.

Especially preferred inhibitor compounds for use in the methods of the invention are L-1-phenyl-2-decanoylamino-3-morpholino-1-propanol (L-PDMP) and trans-1-pyrrolidino-2-hexadecanoylamino-3-hydroxyoctadec-4,5-ene.

Other suitable GalT-2 enhancing compounds can be readily identified by simple testing, e.g. by in vitro testing of a candidate GalT-2 enhancing compound relative to a control for the ability to promote GalT-2 activity, e.g. by at least 10% more than a control.

The invention further relates to methods of detecting and analyzing compounds that promote GalT-2 activity and exhibit therapeutic capacity to treat or prevent the above-described conditions. Preferred detection and analysis methods include both in vitro and in vivo assays to determine the therapeutic capacity of agents to modulate LacCer-responsive cells.

Preferred in vitro detection assays according to the present invention involve one or more steps associated with LacCer-related pathways. Such assays include the following steps 1) through 4):

1) culturing a population of LacCer-responsive cells with LacCer;
2) adding a known or candidate GalT-2 enhancing compound to the cells;
3) measuring activity of a cell molecule or function in the LacCer-related pathway; and
4) determining the effect of the known or candidate GalT-2 enhancing compound on the cell, e.g., by measuring activity of the cell molecule or function. Typically, the cell function will be one or more of cell proliferation, cell adhesion or expression of specified surface proteins on the cells. Examples of cell molecules include LacCer-responsive enzymes as specified below.

That assay can effectively measure the capacity of the GalT-2 enhancing compound to promote GalT-2 activity. References herein to a "standard in vitro GalT-2 assay" or other similar phrase refers to the above protocol of steps 1) through 4) when the specified cell molecule measured in step 3) above is GalT-2. As described in more detail below, other in vitro assays of the invention measure specified cell molecules in the LacCer-related steps or pathways. The in vitro assays of the present invention can be conducted with nearly any population of cells responsive to LacCer as provided below.

Suitable LacCer responsive cells that may be used or tested for compatibility with the standard in vitro GalT-2 assay include cells associated with vascular intima, particularly endothelial and smooth-muscle cells; kidney cells, neurons, glia as well as certain immune cells such as leukocytes. The cells may be immortalized, cultured or may be primary cells as desired. Additionally, tissue slices or organs may also be used.

Although it is generally preferred that whole cells be used in the assay, in some instances a lysate of such cells or tissue, or a substantially purified fraction of the lysate may be employed. Preferred LacCer lysates or subcellular fractions include GalT-2.

The in vitro detection assays of the invention can be adapted in accordance with intended use. For example, as noted above, it has been found that LacCer manifests changes in certain cell functions such as cell proliferation and cell adhesion. Thus, the standard in vitro GalT-2 assay above can be modified, (e.g., at step 3) to include measuring an increase in cell proliferation or adhesion (or both) in response to the added LacCer, and to determine any effect of the GalT-2 enhancing compound on the cell function. The known or candidate GalT-2 enhancing compound tested in the assay can be employed as a sole active agent or in combination with other agents including other GalT-2 enhancing compounds to be tested. In most instances, the in vitro assays are performed with a suitable control assay usually comprising the same test conditions as in the steps above, but without adding the GalT-2 enhancing compound to the medium. In such cases, a candidate GalT-2 enhancing compound can be identified as exhibiting desired activity by exhibiting at least about 10 percent greater activity relative to the control; more preferably at least about 20% greater activity relative to the control assay; and still more preferably at least about 30%, 40%, 50%, 60%, 70, 80%, 100%, 150% or 200% greater activity or more relative to the control.

The invention also provides assays to detect a LacCer-responsive cell which cells may be used, e.g., in an assay of the invention as described herein. In one assay, a potentially LacCer-responsive cell can be contacted by LacCer and then a desired cell molecule or function can be measured as a function of the amount of LacCer added. In most cases, the cell is deemed responsive to LacCer if the assay employed shows at least about 10%, preferably at least about 20%, more preferably at least about 50%, and still more preferably at least about 75% or 100% change in the activity of the molecule or cell function (relative to a control) as determined by the assays provided herein. The assays can be used to identify LacCer-responsiveness in a variety of cells or tissues, including cultured cells (i.e., primary cells or immortalized cell lines), tissue slices and organs.

The in vitro assays are particularly useful for detecting potential synergistic effects between a known or candidate GalT-2 enhancing compound and one or more other molecules, e.g, other GalT-2 enhancing compounds that can increase cell proliferation or adhesion. Examples of such potential molecules include growth factors, cytokines, polypeptides, peptides and particularly peptide hormones, and small molecules such as cyclic nucleotides and certain nucleosides.

The invention also provides in vivo assays to determine the therapeutic capacity of a known or candidate GalT-2 enhancing compound to modulate cell functions impacted by LacCer, e.g. cell proliferation, cell adhesion or both. The monitored cell function suitably may be pre-existing in the test animal, or the cell function may be induced, e.g., by administering a drug capable of modulating the cell function or by conducting an invasive surgical procedure such as angioplasty. In addition to cell proliferation and adhesion, cell functions that can be suitably assayed include, e.g., vessel remodeling, angiogenesis, regeneration of cells and tissue including particularly, tissue repair, and immune responses, e.g., recruitment of specified immune cells such as B and T cells.

Further suitable in vivo assays include those designed to evaluate overall neurological function in a test animal according to conventional methods. For example, the therapeutic capacity of a desired, known, or GalT- enhancing candidate compound can be tested by evaluating CNS and/or PNS function in the test animal. Such tests are known in the field and include those tests that are capable of measuring perception, cognition, motor skills (e.g., reflexes) and vision.

The in vivo assays of the present invention can be modified in a number of ways as needed. For example, in certain embodiments of the present invention relating to measuring vessel cell proliferation, a vessel subjected to analysis can be assayed in vitro following removal from the animal or assayed in vivo if desired. In most embodiments, activity of the GalT-2 enhancing compound in a given in vivo assay is compared to a suitable control (e.g., a sham-operated animal) in which the assay is conducted the same as the test assay but without administering the GalT-2 enhancing compound to the test subject. A variety of test subjects can be employed, particularly mammals such as rabbits, primates, various rodents and the like.

As noted above, the detection assays (either in vitro or in vivo) can be conducted in a wide variety of LacCer-responsive cells, tissues and organs. Further, the assays can detect useful GalT-2 enhancing compounds by measuring the activity of target molecules and/or functions related to the LacCer-related pathways. Thus, the present assays can measure activity in several cell, tissue and organ settings.

Significantly, use of multiple detection assays (e.g., a combination of the in vitro and/or in vivo assays) with a single GalT-2 enhancing compound can extend the selectivity and sensitivity of detection as desired.

Such broad spectrum testing provides additional advantages. Thus, for example, in vitro assays of the invention can efficiently perform multiple analyses, thereby increasing efficiency and probability of identifying GalT-2 enhancing compounds with therapeutic capacity. This is especially useful when large numbers of compounds need to be tested. For instance, libraries of GalT-2 enhancing compounds can be made by standard synthetic methods including combinatorial-type chemistry manipulations and then tested in accord with the invention.

Additionally, many of the LacCer-related steps are "downstream" of GalT-2, and therefore the assays include molecules and cell functions that are active downstream of GalT-2. Accordingly, modest but significant changes in GalT-2 activity can be registered as readily testable signals.

Other aspects of the invention are discussed below.

DETAILED DESCRIPTION OF THE INVENTION

Figure 1:
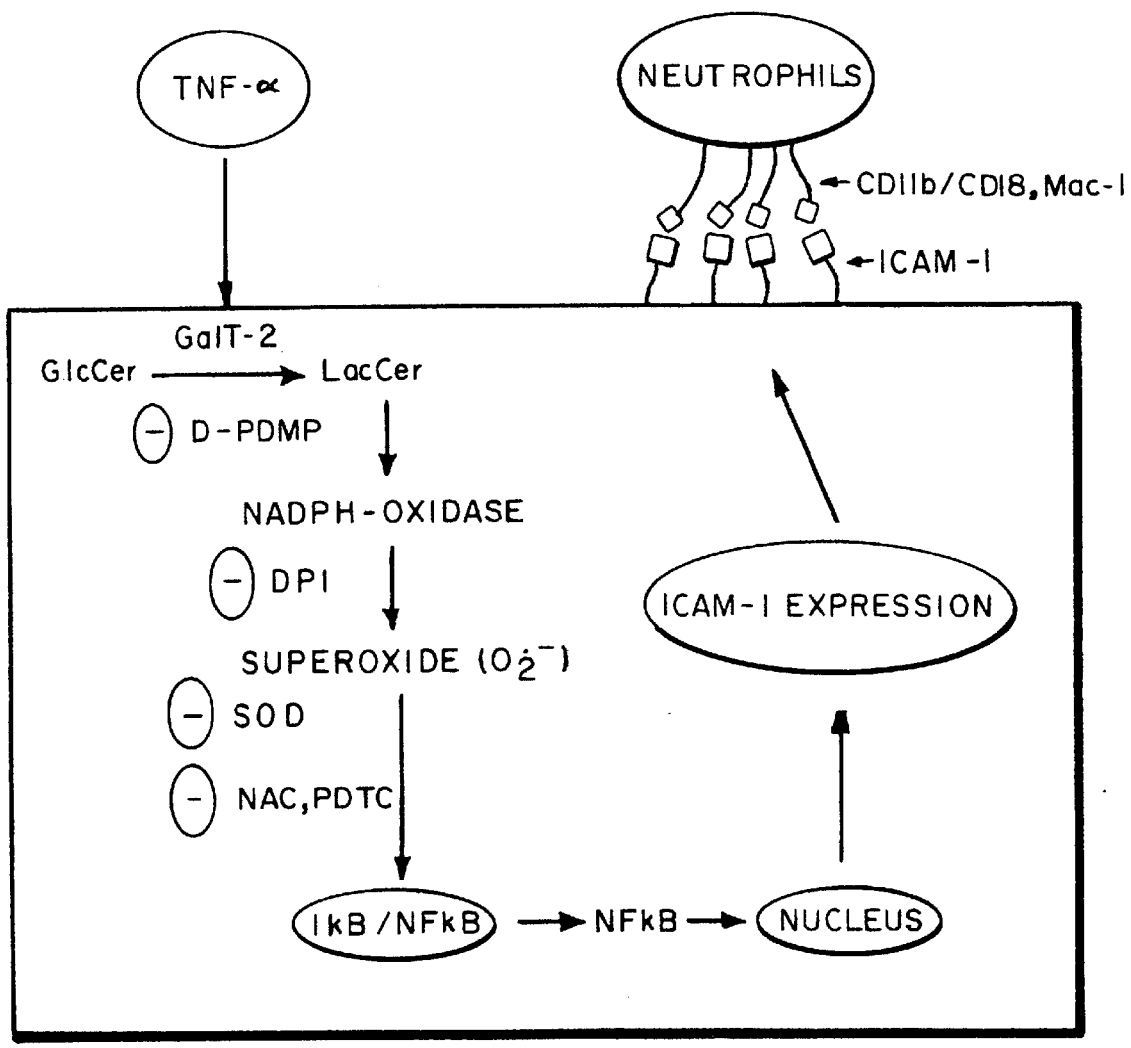
FIG. 1 is a model depicting LacCer-mediated redox signaling leading to ICAM-1 expression in endothelial cells and adhesion to neutrophils.
Figure 2:
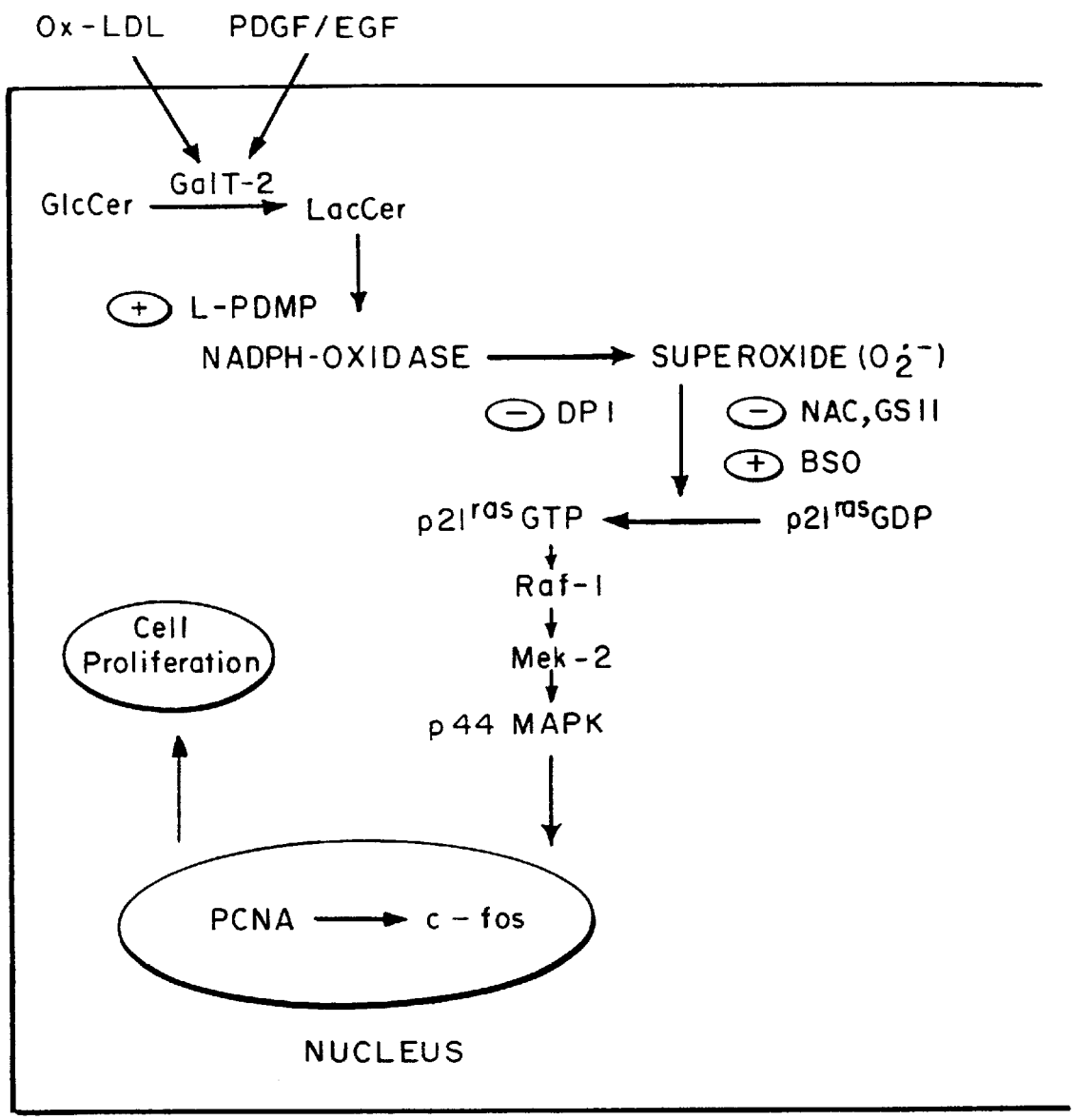
FIG. 2 is a model depicting utilization of Ox-LDL, LacCer, and lipid second messenger in the proliferation of H-ASMC.
Figure 3:
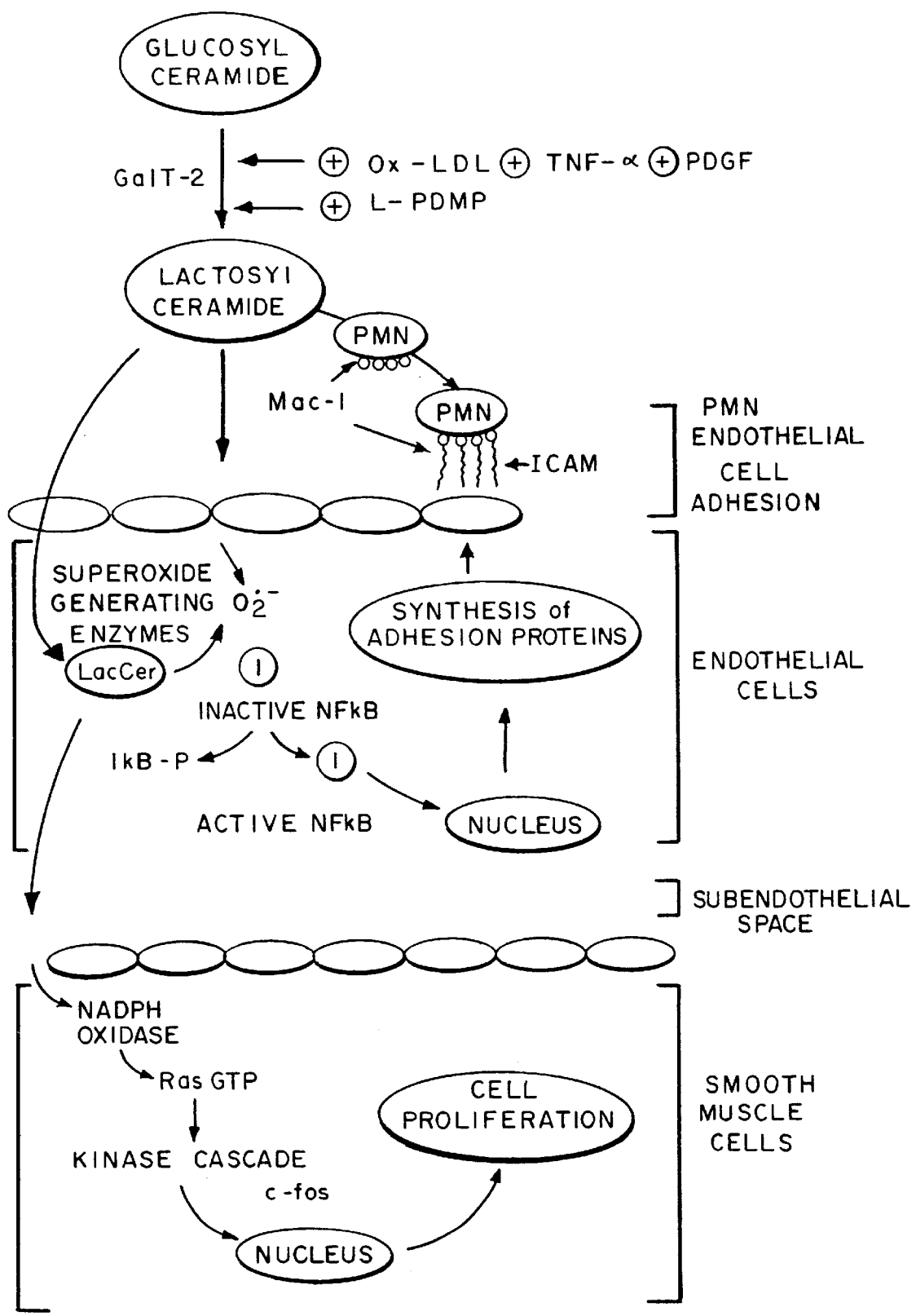
FIG. 3 is a model depicting the role of LacCer as a lipid second messenger and effect of relationship of L-PDMP to abrogate this phenomenon.

As discussed above, the present invention features therapeutic methods for treatment and prevention of conditions modulated by LacCer and particularly those conditions impacted by deficient cell proliferation or adhesion. The treatment methods of the invention generally include administering a therapeutically effective amount of a GalT-2 enhancing compound to a subject, preferably to a patient in need of such treatment.

In co-pending U.S. application Ser. No. 08/998,262 filed on Dec. 24, 1997 and PCT Application PCT/US98/09958, it was disclosed that LacCer is a cell signaling molecule that can modulate various diseases, post-surgical disorders and particularly, restenosis and bacterial infections. That is, it was found that changes in cell levels of LacCer alter the development or severity of those conditions. More particularly, it was found that in LacCer-responsive cells, LacCer functions as a signal molecule to effect changes in certain cell steps (sometimes referred to herein as "LacCer-related steps" or "-related pathways"). It was further disclosed that LacCer-related pathways impact a variety of functions such as cell proliferation and adhesion. The disclosures of the co-pending U.S. application Ser. No. 08/998, 262 filed on Dec. 24, 1997 and corresponding PCT Application PCT/US98/09958 are each incorporated herein by reference in their entirety.

The co-pending U.S. application Ser. No. 08/998,262 further discloses methods for inhibiting the activity of GalT-2 by contacting the GalT-2 or LacCer-responsive cell with an effective amount of a GalT-2 inhibitor compound such as D-PDMP. Further described are therapeutic methods of inhibiting unwanted cell proliferation by administering a therapeutically effective amount of a specified GalT-2 inhibiting compound. In accord with the present invention, it has been found that certain L-enantiomers of D-PDMP (e.g., L-PDMP) are capable of effectively stimulating GalT-2 and increasing proliferation and adhesion in LacCer-responsive cells.

The therapeutic methods of the invention generally comprise administration of a therapeutically effective amount of a GalT-2 enhancing compound to a subject in need of such treatment, such as a mammal, and particularly a primate such as a human. Treatment methods of the invention also comprise administration of an effective amount of a compound of Formula I as defined herein to a subject, particularly a mammal such as a human in need of such treatment for an indication disclosed herein.

Typical subjects include mammals suffering from or susceptible to those conditions discussed above, i.e. conditions whose development or severity can be treated or prevented by increasing the proliferation, chemoattraction or adhesion of certain cells. Illustrative of such conditions include tissue repair following wounding (e.g., after surgery, after thermal exposure such as burning, or grafting) and/or loss of skin due to environmental hazards such as heat or cold stress, UV light or other radiation, chemicals, etc.; vascular malformation particularly in embryos or juvenile animals; angiogenesis; and vasculogenesis. Also contemplated are diseases impacted by deficient cell proliferation or adhesion such as blood coagulation disorders, ulcers such as diabetic and decubitus ulcers; neurodegenerative disorders such as Huntington's disease, amyotrophic lateral schlerosis (ie. ALS or "Lou Gehrig's Disease"), Alzheimer's disease, Parkinson's disease, severe seizure disorders including epilepsy, familial dysautonomia, and ishemia-related disorders. Particular neurodegenerative disorders that can be treated or prevented in accord with the invention include those impacting the eye, e.g, Fuch's dystrophy, Leber's congenital amaurosis, cone/rod dystrophies, central areolar choroidal sclerosis, gyrate atrophy, choroideremia, retinitis pigmentosa, and age-related macular dystrophies, particularly those macular pathologies afflicting the elderly.

A variety of GalT-2 enhancing compounds can be employed in the present treatment methods. Simple testing, e.g., in a standard in vitro assay as defined above, can readily identify suitable GalT-2 enhancing compounds. Preferred GalT-2 enhancing compounds include those that contain a propanol backbone. Generally preferred for use in the treatment methods of the invention are levrorotatory compounds of the following Formula I:

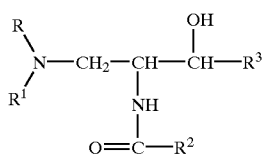

wherein R and $R^1$ are independently selected from the group consisting of hydrogen and straight-chained or branched $C_1$–$C_6$ alkyl with or without a substituent such as amino, hydroxy or mercapto and further wherein R and $R^1$ may be taken together to form a 5, 6 or 7-membered ring substituent such as pyrrolidino, morpholino, thiomorpholino, piperidino, azacycloheptyl and the like;

$R^2$ is selected from the group consisting of branched or straight-chained $C_6$–$C_{30}$ alkyl with or without one to three double bonds; and $R^3$ is selected from the group consisting of straight-chained or branched $C_6$–$C_{20}$ alkyl with or without one to three double bonds and aryl such as carbocyclic aryl (e.g., phenyl), or substituted aryl such as carbocyclic aryl (e.g., phenyl), where the substituent is halo, $C_1$–$C_4$ alkoxy, methylenedioxy, $C_1$–$C_4$ mercapto, amino or substituted amino in which the amino substituents may suitably be $C_1$–$C_4$ alkyl.

Suitable compounds of Formula I above and other GalT-2 enhancing compounds can be readily prepared by known procedures or can be obtained from commercial sources. See, for example, Abe, A. et al., (1992) *J. Biochem.* 111:191–196; Inokuchi, J. et al. (1987) *J. Lipid Res.* 28:565–571; Shukla, A. et al. (1991) *J. Lipid Res.* 32:73; Vunnam, R. R. et al., (1980) *Chem. and Physics of Lipids* 26:265; Carson, K. et al., (1994) *Tetrahedron Lets.* 35:2659; and Akira, A. et al., (1995) *J. Lipid Research* 36:611 and Chatterjee, Supra.

As noted previously, the term "levrotatory" is used herein to describe compounds represented by Formula I above which have capacity to rotate polarized light in the L or (−) direction, i.e., counterclockwise. Rotation of polarized light is usually measured by use of a polarimeter and is most often expressed as degrees of specific rotation (ie. [α]D). The specific rotation of any compound represented by Formula I above is defined herein as the observed rotation of plane polarized light at 589 nm (sodium D line) in a sample path (1 decimeter in length) and a sample concentration of (1 g/mL). A variety of optically inactive solvents may be used as suitable controls such as water or acetone. See McMurry, J. in *Organic Chemistry* 3$^{rd}$ Ed (1992) Brooks Cole Publishing Co., Pacfic Grove, Calif.

In the therapeutic methods of the invention, a treatment compound can be administered to a subject in any of several ways including intracorporeally or topically. Additionally, a GalT-2 enhancing compound can be administered as a prophylactic to prevent the onset of or reduce the severity of a targeted condition. Alternatively, a GalT-2 enhancing compound can be administered during the course of a targeted condition e.g., to help alleviate symptoms.

A treatment compound can be administered to a subject, either alone or in combination with one or more therapeutic agents, as a pharmaceutical composition in mixture with conventional excipient, i.e. pharmaceutically acceptable organic or inorganic carrier substances suitable for parenteral, enteral or intranasal application which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

Such compositions may be prepared for use in parenteral administration, particularly in the form of liquid solutions or suspensions; for oral administration, particularly in the form of tablets or capsules; intranasally, particularly in the form of powders, nasal drops, or aerosols; vaginally; topically e.g. in the form of a cream; rectally e.g. as a suppository; etc.

The pharmaceutical agents may be conveniently administered in unit dosage form and may be prepared by any of the methods well known in the pharmaceutical arts, e.g., as described in *Remington's Pharmaceutical Sciences* (Mack Pub. Co., Easton, Pa., 1980). Formulations for parenteral administration may contain as common excipients such as sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of certain GalT-2 enhancing compounds.

Other potentially useful parenteral delivery systems include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, methoxysalicylate for rectal administration, or citric acid for vaginal administration. Other delivery systems will administer the therapeutic agent(s) directly at a surgical site, e.g. after balloon angioplasty a GalT-2 enhancing compound may be administered by use of stents.

Intraocular administration can be performed as needed e.g., by implanting a device capable of releasing one or more GalT-2 enhancing compounds. See e.g., U.S. Pat. No. 5,618,553 for disclosure relating to intraocular implant devices.

A GalT-2 enhancing compound can be employed in the present treatment methods as the sole active pharmaceutical agent or can be used in combination with other active ingredients, e.g., growth factors such as platelet derived growth factor (PDGF), epidermal growth factor (EGF), fibroblast growth factor (FGF); neurotrophins, e.g., nerve growth factor (NGF); a cytokine; and certain low density proteins such as Ox-LDL and/or oxidized phosphotidylcholine derivatives such as 1-palmitoyl-2-(5-oxovaleryl)-sn-glycerol-3-phosphocholine (POVPC) derivative from minimally modified ADC.

The concentration of one or more treatment compounds in a therapeutic composition will vary depending upon a number of factors, including the dosage of the GalT-2 enhancing compound to be administered, the chemical characteristics (e.g., hydrophobicity) of the composition employed, and the intended mode and route of administration. In general terms, one or more than one of the GalT-2 enhancing compounds may be provided in an aqueous physiological buffer solution containing about 0.1 to 10% w/v of a compound for parenteral administration.

It will be appreciated that the actual preferred amounts of active compounds used in a given therapy will vary according to e.g. the specific compound being utilized, the particular composition formulated, the mode of administration and characteristics of the subject, e.g. the species, sex, weight, general health and age of the subject. Optimal administration rates for a given protocol of administration can be readily ascertained by those skilled in the art using conventional dosage determination tests conducted with regard to the foregoing guidelines. Suitable dose ranges may include from about 1 $\mu$g/kg to about 100 mg/kg of body weight per day.

Therapeutic compounds of the invention are suitably administered in a protonated and water-soluble form, e.g., as a pharmaceutically acceptable salt, typically an acid addition salt such as an inorganic acid addition salt, e.g., a hydrochloride, sulfate, or phosphate salt, or as an organic acid addition salt such as an acetate, maleate, fumarate, tartrate, or citrate salt. Pharmaceutically acceptable salts of therapeutic compounds of the invention also can include metal salts, particularly alkali metal salts such as a sodium salt or potassium salt; alkaline earth metal salts such as a magnesium or calcium salt; ammonium salts such an ammonium or tetramethyl ammonium salt; or an amino acid addition salts such as a lysine, glycine, or phenylalanine salt.

Preferred GalT-2 enhancing compounds exhibit significant activity in a standard cell proliferation assay. Preferably, the GalT-2 enhancing compound promotes cell proliferation by at least 10 to 25%, preferably at least about 50%, relative to a suitable control assay. In such an assay, between about 0.1 to 100 $\mu$M, preferably between about 1 to 50 $\mu$M of a desired GalT-2 enhancing compound is used. Exemplary cell proliferation assays include counting viable cells and monitoring activity of specified citric acid cycle enzymes such as lactate dehydrogenase. A preferred assay measures incorporation of one or more detectably-labeled nucleosides into DNA, e.g., by:

a) culturing suitable cells in medium and adding 1) a candidate GalT-2 enhancing compound and 2) a radiolabeled nucleoside such as $^3$H-thymidine typically in an amount between about 0.1 to 100 $\mu$Ci;

b) incubating the cells, e.g., for about 6–24 hours, and typically followed by washing; and c) measuring incorporation of the radiolabeled nucleoside into DNA over that time relative to a control culture that is prepared and incubated under the same conditions as the assay culture but does not include the potential GalT-2 enhancing compound. The measurement can be achieved by several methods including trichloroacetic acid (TCA) precipitation of labeled DNA on filters followed by scintillation counting. See e.g., Chatterjee, S., *Biochem. Biophys. Res Comm.* (1991) 181:554; Chatterjee, S. et al. (1982) *Eur. J. Biochem.* 120:435 for disclosure relating to this assay.

References herein to a "standard in vitro cell proliferation assay" or other similar phrase refer to an assay that includes the above steps a) through c). One preferred example of a cell proliferation assay uses aortic smooth muscle cells (ASMCs), particularly those obtained from a human, cow or a rabbit. A suitable protocol involves preparing ASMCs according to standard methods and culturing same in microtitre plates in a suitable medium such as Ham's F-10. A desired GalT-2 enhancing compound is then diluted in the medium, preferably to a final concentration of between about 1 to 100 µg, more preferably between about 1 to 50 µg per ml of medium or less followed by an incubation period of between about 1–5 days, preferably about 1 day or less. Following the incubation, a standard cell proliferation can be conducted, e.g., incorporation of tritiated thymidine or lactate dehydrogenase assay as mentioned above. The assays are preferably conducted in triplicate with a variation of between 5% to 10%. See e.g., Ross, R. *J. Cell. Biol.* (1971) 50:172; Chatterjee, S. et al. (1982) *Eur. J. Biochem.* 120:435; Bergmeyer, H. V. In *Principles of Enzymatic Analysis.* (1978) Verlag Chemie, NY; and the co-pending U.S. application Ser. No. 08/998,262 filed on Dec. 24, 1997 and PCT Application PCT/US98/09958.

Additionally, preferred GalT-2 enhancing compounds exhibit significant activity in a conventional cell adhesion assay. Preferably, the GalT-2 enhancing compound increases cell adhesion by at least 25%, preferably at least 50% or more relative to a suitable control assay. In such an assay, between about 0.1 to 100 µM, preferably between about 1 to 50 µM of a desired GalT-2 enhancing compound is used. For example, a preferred cell adhesion assay includes the following steps:
   a) labeling a first population of immune cells, preferably certain leukocytes, with a detectable label which can be a chromatic, radioactive, luminescent (e.g., fluorescent, or phosphorescent), or enzymatic label capable of producing a detectable label,
   b) contacting the first population of cells with a second population of endothelial cells detectably-labeled, e.g., with a chromatic, radioactive, luminescent (e.g., fluorescent or phosphorescent), or enzymatic label preferably different from the label employed in step a); and
   c) detecting any adhesion between the first and second population of cells.

References herein to a "standard in vitro cell adhesion assay" or other similar phrase refer to an assay that includes the above steps a) through c). The detection in step c) can be achieved by a variety of methods such as microscopy (by manually counting cells), particularly confocal microscopy and fluorescence-based photomicroscopy involving FACS; automated cell sorting techniques, immunological methods such as ELISA and RIA; and scintillation counting. See examples below and in the co-pending U.S. application Ser. No. 08/998,262 filed on Dec. 24, 1997 and PCT Application PCT/US98/09958 for disclosure relating to preferred cell adhesion assays.

A preferred in vitro cell adhesion assay measures polymorphonuclear leukocytes (PMNs and/or monocytes) or platelets and increased endothelial cell adhesion before, during or after contact with a desired GalT-2 enhancing compound. The PMNS or monocytes can be collected and purified according to standard methods detailed below. The PMNs or monocytes are then labeled by incubation with a suitable fluorescent dye such as fluorescent Cell Tracker dye (e.g., green) or Calcein-AM. At about the same time, an endothelial cell monolayer prepared in accordance with standard cell culture methods on a suitable substrate such as a slide or a sterilized plastic petri dish is contacted by the GalT-2 enhancing compound washed and labeled with another fluorescent dye such as fluorescent Cell Tracker dye (e.g., orange). The PMNs or monocytes and endothelial cells are then incubated for between about 10 minutes to a few hours, preferably about 30 minutes at 37° C. Non-adherent cells are then washed away from the slide with a physiologically acceptable buffer such as phosphate-buffered saline (PBS). Adhering cells are then quantitated by standard methods such as by use of a fluorescence plate reader. The number of adherent cells on the slide can be quantitated in several ways including expressing the number of PMN/mm$^2$ on the endothelial cell monolayer. Alternatively, the adhering cells can be quantitated by inspection following photomicroscopy and can be visualized and photographed by microscopy. Cell adherence is then evaluated by inspection of the photomicrograph. See the examples which follow.

Particularly preferred are GalT-2 assays conducted with the ASMCs and performed in general accordance with previously described methods. See e.g., Chatterjee, S., and Castiglione, E. (1987) *Biochem. Biophys. Acta*, 923:136; and Chatterjee, (1991) S. *Biochem. Biophys. Res Comm.*, 181:554.

Additionally preferred in vitro cell adhesion assays include immunological detection of adhesion molecules on PMNs using specified antibodies, particularly monoclonals, capable of specifically binding the adhesion molecules. A particularly preferred assay involves flow cytometry.

The in vitro adhesion assays described above are compatible with analysis of a variety of specified adhesion molecules such as ICAM-1 (intracellular adhesion molecule 1), Mac-1 (CD11b/CD18), LFA-1 and E selectin.

Another preferred in vitro assay of the invention specifically monitors LacCer formation as being indicative of Galt-2 enzyme activity and includes the following steps a) through d):
   a) culturing a population of LacCer-responsive cells preferably to confluency in lipoprotein-deficient serum medium, e.g., about 1 mg lipoprotein-deficient serum/ protein/ml of medium or less;
   b) harvesting the cells preferably in a suitable dispersive buffer, e.g., cacodylate buffer;
   c) incubating the harvested cells preferably with a detectably-labeled molecule such as a detectably-labeled nucleoside diphosphate sugar donor such as [$^{14}$C]-UDP-galactose typcially in an amount between about 0.1 to 100 µCi; and
   d) measuring LacCer formation as indicative of the activity of the GalT-2 enzyme.

The assay of the steps a) through d) above is sometimes referred to herein as a "GalT-2 enzyme assay" or similar term. Preferably, the GalT-2 enhancing compound increases the activity of the GalT-2 enzyme by at least about 10% preferably at least about 25%, 50% 75% or more relative to a suitable control assay.

Further preferred GalT-2 enhancing compounds include those that exhibit at least a 2- to 5-fold greater increase in GalT-2 activity relative to GlcT-1 as measured by the GalT-2 enzyme assay or conventional GlcT-1 enzyme assays. More preferred are those GalT-2 enhancing compounds that exhibit at least about 5- to 10-fold greater increase in GalT-2 activity relative to enhancement of GlcT-1, even more preferably at least about 10- to 50-fold. Methods for measuring GlcT-1 activity have been reported. See e.g., Carson, K., and Ganem, B. supra; Shukla, A. and Radin, N. S. *J. Lipid. Res.* 32:713.

Particularly preferred GalT-2 enhancing compounds include those that are capable of specifically enhancing activity of the GalT-2 enzyme. That is, the identified GalT-2 enhancing compound provides relatively poor stimulation of other enzymes such as hydroxyceramide galactosyltransferase, glucocerebroside glucosidase, and particularly GlcT-1. Significantly, the GalT-2 enhancing compound should avoid undesired pharmacological effects that could arise from non-selective inhibition of other GSL-related enzymes. Exemplary of such preferred GalT-2 enhancing compounds are those which potentiate or otherwise stabilize formation of a GalT-2 transition state.

In most instances, the assays generally described above will use known LacCer-responsive cells and will be cultured in a medium suitable for maintaining those cells in the assay, e.g., Eagles's minimum essential medium (HMEM) or Ham's F-10 medium.

The in vivo assays of the invention are particularly useful for subsequent evaluation of GalT-2 enhancing compounds exhibiting suitable activity in an in vitro assay such as those described above. A rabbit model of restenosis accompanying an invasive surgical procedure such as balloon angioplasty is preferred. One suitable protocol involves administering to the animal a suitable vehicle or vehicle combined with one or more GalT-2 enhancing compounds of interest. The amount of the GalT-2 enhancing compound administered will vary depending on several parameters including the extent of damage associated with the surgical procedure of interest. In instances where balloon angioplasty is employed, the rabbit will typically receive a candidate GalT-2 enhancing compound in a dose (e.g., i.m. or i.p.) of between about 0.5 to 100, preferably 1 to 20 and more preferably about 10 mg/kg body weight of the rabbit. A preferred dosage schedule provides for administration of a GalT-2 enhancing compound starting 24 hours prior to conducting an invasive surgical procedure, and then continuing administration of the GalT-2 enhancing compound for 15 days following the surgical procedure. In other protocols, daily injections of the GalT-2 enhancing compound may be made for about 2 to 12 weeks following the invasive surgical procedure. Daily injections, e.g., i.m. or i.p., of the GalT-2 enhancing compound are generally preferred. Subsequently, the rabbits are euthanized and a vessel removed for examination, preferably the aorta. The vessel is then fixed with formalin and analyzed for proliferation of vascular endothelia, media and advantitia using standard histological procedures. Preferably, administration of the GalT-2 enhancing compound will increase intimal cell proliferation, e.g., SMCs epithelia or related cells by at least about 10%, 20%, 40%, 50%, 70%, 100% up to about 200% or greater in this assay.

The term "invasive surgical procedure" means a medical or veterinary technique associated with significant damage to the endothelium of a vessel impacting, e.g., an organ such as the heart, liver or the kidney, or a limb. Such a vessel comprises the aorta, coronary vessel, femoral and iliac arteries and veins. The invasive surgical procedure can be associated with techniques involving, e.g., cardiac surgery, abdominothoracic surgery, arterial surgery, deployment of an implementation (e.g., a vascular stent or catheter), or endarterectomy. A preferred invasive surgical procedure is angioplasty, particularly balloon angioplasty. Preferably, the invasive surgical procedure is performed on a mammal such as a primate, particularly a human, rodent or a rabbit, or a domesticated animal such as a pig, dog or a cat.

Angiogenesis and related processes are believed to involve significant cell proliferation, particularly of SMCs, leading to formation of endothelial cell sprouts and vascular loops. Additionally preferred assays are those capable of monitoring angiogenesis before and after administration of a compound in accord with this invention. In particular, angiogenesis can be evaluated and quantified (if desired) by use of previously characterized animal models of hindlimb ischemia. Additionally known animal models related to quantitative monitoring of angiogenesis are those involving vessel damage inflicted by invasive surgery as described above. In particular, conventional methods of angiographic quantitation of femoral and other large arteries are known in the field and can be performed in rodents and other animal models. See e.g., LeFree, et al. *Proc. SPIE*, 626: 334–331 (1986); Mancini, et al. *Circulation*, 75: 452–460 (1987); and Folkman J. et al. *J. Biol. Chem.* 267L: 10931 (1992) and references cited therein for disclosure relating to these methods. Preferred GalT-2 enhancing compounds are capable of increasing angiogenesis as measured, e.g., by evaluating angiographic luminal diameters, by at least about 5%, preferably 10%, 20%, 50%, up to about 100% when compared to a suitable control.

Enhancement of angiogenesis has been reported to beneficial in the treatment or prevention of a variety of conditions such as cerebrovascular ischemia, renal ischemia, pulmonary ischemia, limb ischemia, ischemic cardiomyopathy, myocardial ischemia and related conditions. Accordingly, the GalT-2 enhancing compounds of this invention are useful in the treatment or prevention of these and related conditions.

Additionally preferred in vivo assays are those which measure function of the CNS and/or PNS of test animals such as a primate, rodent, rabbit and the like. For example, perception, cognition, and vision can be measured by a variety of conventional methods in animal models and particularly in human patients. In particular, macular degeneration in the eye can be monitored and quantitated if desired by a well-known photographic tests, e.g., fundus photography, fluorescein angiography, and the like to grade macular lesions before and after administration of a desired GalT-2 enhancing compound. Additional well-known tests such as macular recovery function assays, central visual field sensitivity, spatiotemporal contrast sensitivity, and the Farnsworth-Munsell 100 hue test can be performed to evaluate efficacy of the compounds in patients.

As noted above, the present invention includes methods of detecting and analyzing GalT-2 enhancing compounds with therapeutic capacity to treat or prevent any of the above-mentioned conditions modulated by LacCer. A disease is suitably considered as being modulated by LacCer if afflicted cells or tissue increase. GalT-2 activity about 2- to 50-fold, typically about 2- to 10-fold, and more typically about 2- to 5-fold higher than that of control (unafflicted) cells or tissue. The GalT-2 activity can be measured by methods referenced herein. Without being bound by theory, it appears that increased GalT-2 activity produces substantial amounts of LacCer. That LacCer is believed to enhance the onset of or contribute to the conditions mentioned, particularly by increasing cell proliferation or adhesion.

Generally stated, the novel LacCer-related steps disclosed herein have been found to relate changes in GalT-2 activity to cell proliferation or adhesion in LacCer-responsive cells. It has been determined that the LacCer-related steps can be grouped into those modulating cell proliferation and adhesion. The LacCer-related steps have been found to include a variety of identified molecules such as specified enzymes, cytosolic factors, nuclear factors, radical species and adhesion proteins. More particular examples of such molecules in the LacCer-related biochemical steps include GTP-binding proteins, kinases, cytosolic factors, nuclear factors, transcription factors, and oxygen species, particularly reactive oxygen species (sometimes referred to herein as "ROS" or "ROM").

Detection methods of the invention are formatted to include one or more steps associated with LacCer-related pathways. More particularly, the detection methods include specific steps that measure the activity of molecules which act to modulate cell proliferation or adhesion. In some cases, a particular molecule will act to inhibit both cell proliferation and adhesion through a LacCer-related pathway.

The LacCer-related steps are typically found in cells responsive to LacCer. A LacCer-responsive cell can be an immortalized cell line or primary culture of cells (e.g., obtained form a tissue or organ) that manifests a change in one or more specific cell molecules or functions such as proliferation or adhesion, following contact with a suitable amount of LacCer.

More specifically, one or a combination of strategies can identify a LacCer-responsive mammalian cell. For example, in one approach, about $1\times10^5$ cells are seeded in petri dishes in suitable growth medium. For primary cultures of cells, a desired tissue or organ is obtained from an animal and dispersed according to standard methods (e.g., by sonication, mechanical agitation, and/or exposure to dispersing agents known in the field, e.g., detergents and proteases). After one or a few days, the growth medium is removed from the petri dish and the cells washed with phosphate-buffered saline. The cells are then primed in a suitable medium for about 1 to 5 hours at which point LacCer is added to culture. The amount of LacCer added will depend on several parameters such as the particular cell or tissue type being tested. In most cases however, the LacCer will be added to the culture at a concentration of between about 1 $\mu$g to 1 mg, preferably between about 1 $\mu$g to 500 $\mu$g, and more preferably between about 1 $\mu$g to 50 $\mu$g per ml of culture medium. After exposing the cells to the LacCer for between about 1 to 60 minutes, preferably between about 1 to 10 minutes or less, the medium is removed and the cells lysed in an appropriate lysis buffer such as those described in detail below. The cells are then assayed according to any of the methods described herein for response to the added LacCer.

Particularly preferred LacCer-responsive mammalian cells include cells associated with the vasculature of an organ or limb, particularly heart or kidney cells e.g, endothelial cells and smooth muscle cells. Additionally preferred are neurons and related cells. More particularly, human ASMCs (sometimes referred to herein as H-ASMCs to denote human origin) and endothelial cells. Also preferred are certain immune cells such as white blood cells, particularly PMNs and monocytes.

Preferred GalT-2 enhancing compounds also include those that exhibit good capacity to modulate one or more specified molecules in a LacCer-related step following exposure to LacCer. Particularly preferred compounds exhibit at least 20%, preferably at least 50% and more preferably at least 90% or more of a increase in the activity of the molecule (relative to a suitable control assay) at a concentration of between about 0.1 to 100 $\mu$g/ml, preferably between about 1 to 10 $\mu$g/ml in an in vitro detection assay. The activity of the molecules can increase (or sometimes decrease as described above) in any of several readily detectable ways including altered synthesis, degradation or storage; protein modification, e.g., phosphorylation, or through an allosteric effect as with certain enzymes.

In particular, if the molecule of interest is an enzyme, preferred GalT-2 enhancing compounds include those that exhibit good activity in an enzyme assay as described below. Preferably, an $EC_{50}$ in such an assay is about 1 $\mu$M or less, more preferably an $EC_{50}$ about 0.001 $\mu$M or less.

A control experiment is generally tailored for use in a particular assay. For example, most control experiments involve subjecting a test sample (e.g., a population of LacCer-responsive cells or lysate thereof) to medium, saline, buffer or water instead of a potential GalT-2 enhancing compound in parallel to the cells receiving an amount of test compound. A desired assay is then conducted in accordance with the present methods. Specific examples of suitable control experiments are described below.

The present detection methods also can be used to identify GalT-2 enhancing compounds obtained from biological sources, including specified growth factors, cytokines, polypeptide and peptide hormones and lipoproteins (e.g., Ox-LDL) that modulate GalT-2 activity.

The present detection methods further include assays that measure the activity of specified molecules in LacCer-related biochemical steps. The measurements can be conducted by standard laboratory manipulations such as chemiluminescence tests, thin layer chromatography (TLC) separations or other chromatographic methods such as HPLC, nucleic acid isolation and purification, SDS-PAGE gel electrophoresis, autoradiography, scintillation counting, densitometery, Northern and Western Blot hybridization, and immunoassays (e.g., RIA and ELISA tests). See generally Sambrook et al. in *Molecular Cloning: A Laboratory Manual* (2d ed. 1989); and Ausubel et al. (1989), *Current Protocols in Molecular Biology*, John Wiley & Sons, New York for discussion relating to many of the standard methods, the disclosures of which are incorporated herein by reference.

In one aspect, the present in vitro assays measure the activity of certain enzymes in LacCer-responsive cells. The activity of the enzymes has been found to be modulated following exposure of the cells to LacCer and/or a specified GalT-2 enhancing compound such as L-PDMP, oxidized lipoprotein (ox-LDL), nerve growth factor (NGF), platelet derived growth factor (PDGF), epidermal growth factor (EGF), and tumor necrosis factor-$\alpha$ (TNF-$\alpha$).

In particular, L-PDMP has been found to increase the activity of GalT-2 and can be used to test effect on other enzymes according to the methods described herein. The in vitro assays described herein can be used to test the activity of these enzymes, e.g., specified redox enzymes, nucleotide-binding proteins, and kinases as described below.

For example, one particular in vitro assay in accord with the present invention measures the activity of an oxidase capable of synthesizing an oxygen species, particularly a ROS such as superoxide. A particularly preferred enzyme is NADPH oxidase. The activity of the NADPH oxidase can be assayed by standard methods including fractionating the enzyme from cell components and then measuring the activity by enzyme assay such as those employing a standard chemiluminescence method.

Alternatively, the NADPH oxidase can be assayed by measuring superoxide production in intact cells. Typically, the measurement is conducted in the presence of a mitochondrial poison such as KCN, an enhancing of NADH oxidase. Alternatively, the activity of the NADPH oxidase can be assayed in intact LacCer-responsive cells by measuring superoxide production. The superoxide measurement can be performed in several ways including incubating the cells with a photosensitive polycyclic organic compound (e.g., an acridylium compound). Reduction of the polycyclic compound by superoxide causes light emission that can be detected by a standard photon counter. Preferred methods of measuring the NADPH oxidase activity are described in Bhunia, A. K. et al. (1997) *J. Biol. Chem.* 275:15642.

Additional in vitro assays are provided which measure one or more enzymes that have been found to be modulated by LacCer and GalT-2 enhancing compounds disclosed herein. The enzymes include Ras-GTP-binding protein, Raf-1, mitogen activated protein (MAP) kinase (MEK-2), and other mitogen activated protein kinases such as p44 MAPK. Each of these enzymes can be assayed by one or a combination of conventional methods.

For example, incorporation of a nucleoside triphosphate, particularly a cyclic nucleoside triphosphate such as guanidine nucleoside triphosphate (GTP) into an oncogene protein such as the ras protein (i.e. ras-GTP loading) by the ras-GTP-binding protein can be measured by a number of distinct approaches including direct detection of nucleoside triphosphate (e.g., GTP) incorporation into Ras. For example, in one approach, LacCer-responsive cells are metabolically labeled with radioactive orthophosphate (e.g., $^{32}$P-labeled) to detectably-label the GTP inside the cells. The labeled cells are incubated with LacCer followed by a GalT-2 enhancing compound and then washed and lysed in a suitable lysis buffer such as RIPA (see below). Subsequently, the cell lysate is separated on suitable TLC plates. The TLC plates are exposed to X-ray film and then subjected to densitometery, if desired, to quantitate incorporation of the GTP into the Ras protein. A preferred method for detecting ras-GTP loading has been disclosed in Chatterjee, S. et al., (1997) *Glycobiology*, 7:703.

Methods are also provided for measuring the activity of the Raf-1 and Mek-2 enzymes. For example, in one approach, the LacCer-responsive cells are incubated with LacCer and a potential GalT-2 enhancing compound, washed, and then harvested after about 1 to 60 minutes, preferably 1 to 10 minutes or less, after exposure to the LacCer. Whole cell lysates are prepared and then subjected to standard SDS-PAGE gel electrophoresis. The gels are transferred to a suitable membrane support and then probed with anti-RAF-1 or anti-MEK antibody in accordance with conventional Western blot hybridization procedures. Preferred examples of assays for measuring the Raf-1 and Mek-2 enzymes are disclosed in Bhunia, A. K. et al., (1996) *J. Biol. Chem.*, 271:10660.

Additional in vitro assays are provided which measure activity of DNA binding proteins, e.g., transcription factors such as c-fos, or the nuclear factor kB DNA binding protein (NF-kB). These DNA binding proteins have been surprisingly found to be modulated by LacCer and GalT-2 enhancing compound. The DNA binding proteins can be assayed by a number of conventional approaches.

For example, the activity of the NF-kB DNA binding protein can be measured by a standard polyacrylamide gel mobility shift assay. The gel assay is performed after contacting LacCer-responsive cells with LacCer followed by a potential GalT-2 enhancing compound. A cell lysate is prepared from the LacCer-responsive cells which is then contacted with an oligonucleotide sequence comprising (or consisting of) a recognized NF-kB DNA binding sequence. The reaction mixture is then incubated for a time sufficient to allow the NF-kB protein and the DNA binding sequence to form a specific binding complex. The specific binding complex is then separated on an SDS-PAGE polyacrylamide gel which is subsequently dried and exposed to X-ray film.

Additional in vitro suitable for measuring modulation by LacCer and GalT-2 enhancing compounds include monitoring expression of cell proliferation factors (e.g., cyclin). A preferred proliferating cell factor for such analysis is proliferating cell nuclear antigen (PCNA or cyclin). In one suitable approach, the cultured cells are incubated with LacCer followed by a GalT-2 enhancing compound and then washed with a suitable buffer. PCNA in the cultured cells can be detected (and quantified if desired) by using a monoclonal antibody that is capable of specifically binding the PCNA (e.g., PC10 antibody). See Sasaki, K., et al. (1993) *Cytometry* 14:876–882. The PCNA then can be detected in the cells by a variety of immunological methods including flow cytometery or imunohistochemical visualization of fixed cell sections.

Additionally preferred GalT-2 enhancing compounds are capable of inhibiting activity of and reducing levels of certain globo-series glycosphingolipids particularly GALNac1→3Galα1→4Galβ1→GlcCer (hereinafter "GbOse$_4$ Cer"). Cell levels of GbOse$_4$ Cer can be measured by a variety of methods including the following general method (hereinafter referred to as a "GbOse$_4$ Cer assay"):

a) culturing a population of LacCer-responsive cells (e.g, "human kidney" proximal tubule cells) preferably to confluency in lipoprotein-deficient serum medium, e.g., about 1 mg lipoprotein-deficient serum/protein/ml of medium or less;

b) harvesting the cells, e.g., in a suitable dispersive buffer such as cacodylate buffer; and c) measuring GSLs and particularly GbOse$_4$ Cer as indicative of the capacity of the known or candidate GalT-2 enhancing compound to inhibit N-acetylgalactosaminyltransferase.

The known or candidate GalT-2 enhancing compound can be added at any of the steps a) through c) of the GbOse$_4$ Cer assay, although it is generally preferred that the compound be added during incubation with the lipoprotein-deficient serum medium. The GSLs including GbOse$_4$ Cer can be measured and quantitated by a variety of methods including chromatography, e.g., high performance liquid chromatography (HPLC); along with suitable GSL standards (obtained e.g., from Sigma, St. Louis, Mo.). Preferably, the GalT-2 enhancing compound has an IC$_{50}$ of at least about 10 μM in the GbOse$_4$ Cer assay, more preferably an IC$_{50}$ of about 1 μM or less, still more preferably an IC$_{50}$ of about 0.001 μM or less in the assay. See e.g., Chatterjee, S., et al. (1982); *J. Lipid Res* 23:513–22; Ullman, M. D., et al (1977) *J. Lipid Res.* 18:371–78; BASU, M. et al. (1987) *Methods Enzm.* 138: 575–607; Chatterjee, S. et al. (1988), *J. Bid. Cler* 263:13017–23 and Chatterjee, S. et al. *Glycoconjugate J.* (1996) 13:481–486.

All documents mentioned herein are incorporated by reference herein in their entirety.

The following non-limiting example further illustrates the invention.

EXAMPLE 1

Figure 4:
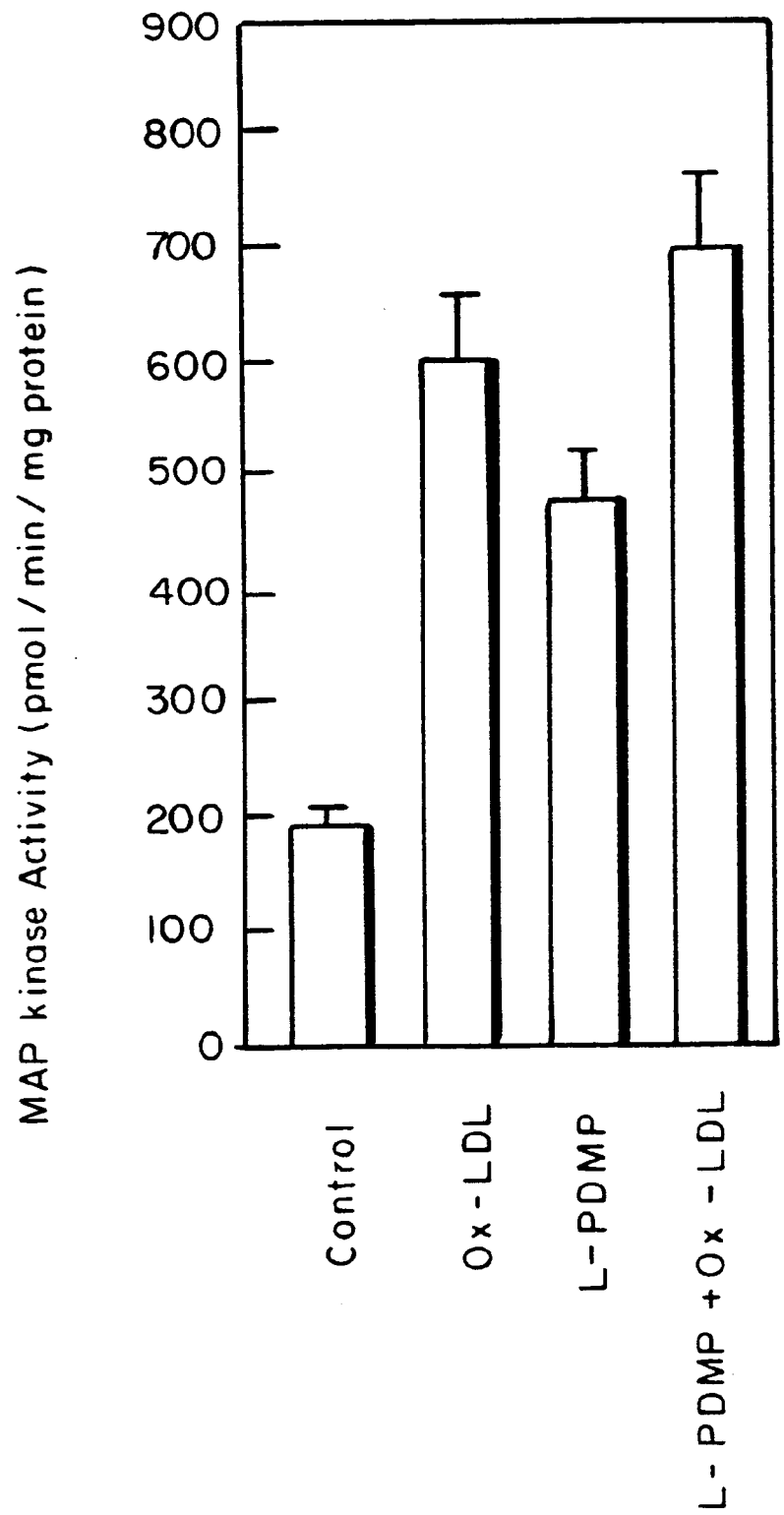
FIG. 4. shows the effect of L-PDMP and Ox-LDL on MAPK activity.

The effects of L-PDMP and Ox-LDL on MAPK activity were examined. Confluent cultures of human aortic smooth muscle cells were preincubated for 2 hours with L-PDMP (10 μM). Next Ox-LDL (10 μg/ml) was added to the cells. After incubation for 10 minuites at 37° C., cells were harvested and MAP kinase activity was measured in the immunoprecipates. Results are shown in FIG. 4 of the drawings. Those results represent +SD values of three separate experiments analyzed in duplicate.

The invention has been described in detail with reference to preferred embodiments thereof. However, it will be appreciated that those skilled in the art, upon consideration of this disclosure, may make modification and improvements within the spirit and scope of the invention as set forth in the following claims.

What is claimed is:

1. A method for treating a condition modulated by lactosylceramide in a mammal suffering from or susceptible to the condition, the method comprising administering to the mammal a therapeutically effective amount of a levorotatory GalT-2 enhancing compound.

2. The method of claim 1 wherein the insufficient cell proliferation is diagnostic of the condition.

3. The method of claim 1 or 2 wherein the condition is any one of nervous system degeneration, a wound, or an ulcer.

4. The method of claim 3, wherein the GalT-2 enhancing compound is co-administered with at least one platelet derived growth factor (PDGF), oxidized low density lipoprotein (ox-LDL), transforming growth factor alpha (TNF-α2) or another GalT-2 enhancing compound .

5. The method of claim 3, wherein the compound enhances cell proliferation by at least 25% in a standard in vitro cell proliferation assay.

6. The method of claim 3, wherein the compound enhances cell adhesion by at least 25% in a standard in vitro cell adhesion assay.

7. The method of claim 3, wherein the compound exhibits an $EC_{50}$ of about 1 μm or less in a standard in vitro GalT-2 enzyme assay.

8. The method of claim 3, wherein the compound exhibits an $IC_{50}$ of about 0.001 μm or less in a standard in vitro $GbOse_4$ Cer assay.

9. The method of claim 3, wherein the compound is levorotatory and is represented by the following Formula I:

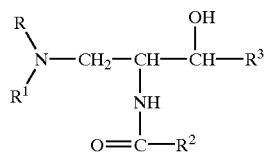

wherein R and $R^1$ are independently selected from the group consisting of hydrogen and straight-chained or branched $C_1$–$C_6$ alkyl with or without a substituent, and further wherein R and $R^1$ are optionally joined to form a 5, 6 or 7-membered ring;

$R^2$ is selected from the group consisting of branched or straight-chained $C_6$–$C_{30}$ alkyl with or without one to three double bonds; and $R^3$ is selected from the group consisting of straight-chained or branched $C_6$–$C_{20}$ alkyl with or without one to three double bonds and aryl or substituted aryl where the substituent is halo, $C_1$–$C_4$ alkoxy, methylenedioxy, $C_1$–$C_4$ mercapto, amino or substituted amino in which the amino substituent is $C_1$–$C_4$ alkyl.

10. The method of claim 9 wherein R and $R^1$ are joined to form a 5, 6 or 7-membered ring.

11. The method of claim 9 wherein R and $R^1$ are joined to form a pyrrolidino, morpholino, thiomorpholino, piperidino or azacycloheptyl ring.

12. The method of claim 3, wherein the compound is levrotatory and is selected from the group consisting of:

1-phenyl-2-decanoylamino-3-morpholino-1-propanol;

1-phenyl-2-hexadecanoylamino-3-morpholino-1-propanol;

1-phenyl-2-hexadecanoylamino-3-piperdino-1-propanol;

1-phenyl-2-hexadecanoylamino-3-pyrrolidino-1-propanol;

1-morpholino-2-hexadecanoylamino-3-hydroxyoctadec-4,5-ene; and 1-pyrrolidino-2-hexadecanoylamino-3-hydroxyoctadec-4,5-ene.

13. The method of claim 3, wherein the compound is L-1-phenyl-2-decanoylamino-3-morpholino-1-propanol (L-PDMP).

14. A method for increasing angiogenesis in a mammal comprising administering to the mammal one or more levorotatory GalT-2 enhancing compounds in an amount sufficient to increase angiogenesis in the mammal.

15. The method of claim 14, wherein the increased cell proliferation is in any one of brain, eye, heart, kidney or vasculature.

16. The method of claim 14, wherein the GalT-2 enhancing compound is administered to the mammal by a stent.

17. The method of claim 14, wherein the GalT-2 enhancing compound is administered to the mammal orally, intramuscularly, topically, intraoculary or intraperitoneally.

18. The method of claim 14, wherein said levorotary GalT-2 enhancing compound is L-phenyl-2-decanolyamino-3-morpholino-1-proponal.

19. The method of claim 14 or 18, wherein said method is used to treat ischemia.

20. The method of any one of claims 1, 2, 14, 15, 16, or 17, wherein the GalT-2 enhancing compound is co-administered with at least one platelet derived growth factor (PDGF), oxidized low density lipoprotein (ox-LDL), transforming growth factor alpha (TNF-α2) or another GalT-2 enhancing compound.

21. The method of any one of claims 1, 2, 14, 15, 16, or 17, wherein the compound enhances cell proliferation by at least 25% in a standard in vitro cell proliferation assay.

22. The method of any one of claims 1, 2, 14, 15, 16, or 17, wherein the compound enhances cell adhesion by at least 25% in a standard in vitro cell adhesion assay.

23. The method of any one of claims 1, 2, 14, 15, 16, or 17, wherein the compound exhibits an $EC_{50}$ of about 1 μm or less in a standard in vitro GalT-2 enzyme assay.

24. The method of any one of claims 1, 2, 14, 15, 16, or 17, wherein the compound exhibits an $IC_{50}$ of about 0.001 μm or less in a standard in vitro $GbOse_4$ Cer assay.

25. The method of any one of claims 1, 2, 14, 15, 16, or 17, wherein the compound is levorotatory and is represented by the following Formula I:

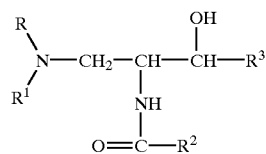

wherein R and $R^1$ are independently selected from the group consisting of hydrogen and straight-chained or branched $C_1$–$C_6$ alkyl with or without a substituent, and further wherein R and $R^1$ may be joined to form a 5, 6 or 7-membered ring;

$R^2$ is selected from the group consisting of branched or straight-chained $C_6$–$C_{30}$ alkyl with or without one to three double bonds; and $R^3$ is selected from the group consisting of straight-chained or branched $C_6$–$C_{20}$ alkyl with or without one to three double bonds and aryl or substituted aryl where the substituent is halo, $C_1$–$C_4$ alkoxy, methylenedioxy, $C_1$–$C_4$ mercapto, amino or substituted amino in which the amino substituent may be $C_1$–$C_4$ alkyl.

26. The method of claim 25 wherein R and $R^1$ are joined to form a 5, 6 or 7-membered ring.

27. The method of claim 25 wherein R and $R^1$ are joined to form a pyrrolidino, morpholino, thiomorpholino, piperidino or azacycloheptyl ring.

28. The method of any one of claims 1, 2, 14, 15, 16, or 17, wherein the compound is levorotatory and is selected from the group consisting of:

1-phenyl-2-decanoylamino-3-morpholino-1-propanol;
1-phenyl-2-hexadecanoylamino-3-morpholino-1-propanol;
1-phenyl-2-hexadecanoylamino-3-piperdino-1-propanol;
1-phenyl-2-hexadecanoylamino-3-pyrrolidino-1-propanol;
1-morpholino-2-hexadecanoylamino-3-hydroxyoctadec-4,5-ene; and
1-pyrrolidino-2-hexadecanoylamino-3-hydroxyoctadec-4,5-ene.

29. The method of any one of claims 1, 2, 14, 15, 16, or 17, wherein the compound is L-PDMP.

30. A method for treating a mammal suffering from or susceptible to insufficient cell proliferation or cell adhesion, comprising administering to the mammal a therapeutically effective amount of a levrorotatory compound of the following Formula I:

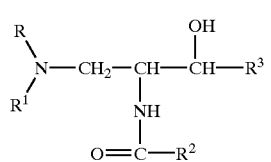

I wherein R and $R^1$ are independently selected from the group consisting of hydrogen and straight-chained or branched $C_1$–$C_6$ alkyl with or without a substituent, and further wherein R and $R^1$ are optionally joined to form a 5, 6 or 7-membered ring;

$R^2$ is selected from the group consisting of branched or straight-chained $C_6$–$C_{30}$ alkyl with or without one to three double bonds; and $R^3$ is selected from the group consisting of straight-chained or branched $C_6$–$C_{20}$ alkyl with or without one to three double bonds and aryl or substituted aryl where the substituent is halo, $C_1$–$C_4$ alkoxy, methylenedioxy, $C_1$–$C_4$ mercapto, amino or substituted amino in which the amino substituent may be $C_1$–$C_4$ alky.

31. The method of claim 30 wherein R and $R^1$ are joined to form a 5, 6 or 7-membered ring.

32. The method of claim 30 wherein R and $R^1$ are joined to form a pyrrolidino, morpholino, thiomorpholino, piperidino or azacycloheptyl ring.

33. The method of claim 30 wherein the levrrotatory compound is selected from the group consisting of L-enantiomers of:

1-phenyl-2-decanoylamino-3-morpholino-1-propanol;
1-phenyl-2-hexadecanoylamino-3-morpholino-1-propanol;
1-phenyl-2-hexadecanoylamino-3-piperidino-1-propanol;
1-phenyl-2-hexadecanoylamino-3-pyrrolidino-1-propanol;
1-morpholino-2-hexadecanoylamino-3-hydroxyoctadec-4,5-ene;
1-pyrrolidino-2-hexadecanoylamino-3-hydroxyoctadec-4,5-ene; and
trans-1-pyrrolidino-2-hexadecanoylamino-3-hydroxyoctadec-4,5-ene.

34. A method for treating a condition modulated by lactosylceramide in a mammal suffering from or susceptible to the condition, the method comprising administering to the mammal a therapeutically effective amount of a levorotatory GalT-2 enhancing compound, wherein the condition is a bacterial infection or atherosclerosis.

35. A method for increasing MAP Kinase activity in a mammal comprising administering to the mammal a therapeutically effective amount of a levorotary GalT-2 enhancing compound.

36. The method according to claim 35, wherein said levorotary GalT-2 enhancing compound comprises L-phenyl-2-decanolyamino-3-morpholino-1-proponal.

* * * * *